(12) United States Patent
Bender et al.

(10) Patent No.: US 7,875,053 B2
(45) Date of Patent: Jan. 25, 2011

(54) APPARATUS AND METHOD FOR CLOSURE OF PATENT FORAMEN OVALE

(75) Inventors: Theodore M. Bender, Oakland, CA (US); Bernard A. Hausen, Redwood City, CA (US); Philipe R. Manoux, San Francisco, CA (US); Bryan D. Knodel, Flagstaff, AZ (US); Joshua M. O. Newth, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 462 days.

(21) Appl. No.: 11/522,217

(22) Filed: Sep. 15, 2006

(65) Prior Publication Data

US 2008/0071294 A1    Mar. 20, 2008

(51) Int. Cl.
*A61B 17/08* (2006.01)
(52) U.S. Cl. ............. 606/213; 606/219; 606/142; 606/143; 606/157
(58) Field of Classification Search ............. 606/139, 606/142, 144, 150, 153, 158; 227/175.1, 227/19, 118.1
See application file for complete search history.

(56) References Cited

U.S. PATENT DOCUMENTS

| | | | |
|---|---|---|---|
| 3,526,228 A | 9/1970 | Lyng | |
| 3,958,576 A | 5/1976 | Komiya | |
| 5,044,540 A * | 9/1991 | Dulebohn | ............... 227/175.1 |
| 5,201,745 A | 4/1993 | Tayot et al. | |
| 5,242,457 A * | 9/1993 | Akopov et al. | ............... 606/144 |
| 5,413,584 A | 5/1995 | Schulze | |
| 5,662,681 A | 9/1997 | Nash et al. | |
| 5,674,231 A | 10/1997 | Green et al. | |
| 5,725,536 A * | 3/1998 | Oberlin et al. | ............... 606/139 |
| 5,792,094 A | 8/1998 | Stevens et al. | |
| 5,843,124 A | 12/1998 | Hammerslag | |
| 5,861,005 A | 1/1999 | Kontos | |
| 5,910,155 A | 6/1999 | Ratcliff et al. | |

(Continued)

FOREIGN PATENT DOCUMENTS

WO    WO-99/62408    12/1999

(Continued)

OTHER PUBLICATIONS

"Notification, International Search Report, and Written Opinion of the International Search Authority", PCT/US2007/077416, (Apr. 11, 2008).

(Continued)

*Primary Examiner*—Darwin P Erezo
*Assistant Examiner*—Alexander Orkin
(74) *Attorney, Agent, or Firm*—Brian A. Schar (57) ABSTRACT

A method for closing a patent foramen ovale in the heart tissue of a patient may include percutaneously advancing a connector applicator to the patent foramen ovale, registering the connector applicator with the patent foramen ovale, deploying connectors into heart tissue to close the patent foramen ovale; and percutaneously removing the connector applicator from the heart. One or more anchors may be used to register the connector applicator with the patent foramen ovale. The connector applicator may include a driver having a longitudinal passage therein, where at least part of at least one connector is positioned within the passage.

8 Claims, 11 Drawing Sheets

U.S. PATENT DOCUMENTS

| | | | |
|---|---|---|---|
| 6,022,372 | A | 2/2000 | Kontos |
| 6,149,660 | A | 11/2000 | Laufer et al. |
| 6,197,042 | B1 | 3/2001 | Ginn et al. |
| 6,277,140 | B2 | 8/2001 | Ginn et al. |
| 6,302,898 | B1 | 10/2001 | Edwards et al. |
| 6,322,580 | B1 | 11/2001 | Kanner |
| 6,348,064 | B1 | 2/2002 | Kanner |
| 6,368,341 | B1 | 4/2002 | Abrahamson |
| 6,371,974 | B1 | 4/2002 | Brenneman et al. |
| 6,391,048 | B1 | 5/2002 | Ginn et al. |
| 6,451,031 | B1 | 9/2002 | Kontos |
| 6,461,364 | B1 | 10/2002 | Ginn et al. |
| 6,482,224 | B1 | 11/2002 | Michler et al. |
| 6,506,196 | B1 * | 1/2003 | Laufer ............... 606/142 |
| 6,506,210 | B1 | 1/2003 | Kanner |
| 6,508,828 | B1 | 1/2003 | Akerfeldt et al. |
| 6,524,321 | B2 | 2/2003 | Kanesaka |
| 6,524,326 | B1 | 2/2003 | Zhu et al. |
| 6,533,762 | B2 | 3/2003 | Kanner et al. |
| 6,540,735 | B1 | 4/2003 | Ashby et al. |
| 6,623,510 | B2 | 9/2003 | Carley et al. |
| 6,626,930 | B1 | 9/2003 | Allen et al. |
| 6,632,238 | B2 | 10/2003 | Ginn et al. |
| 6,676,685 | B2 | 1/2004 | Pedros et al. |
| 6,695,867 | B2 | 2/2004 | Ginn et al. |
| 6,702,825 | B2 * | 3/2004 | Frazier et al. ............. 606/139 |
| 6,719,777 | B2 | 4/2004 | Ginn et al. |
| 6,726,704 | B1 | 4/2004 | Loshakove et al. |
| 6,743,248 | B2 | 6/2004 | Edwards et al. |
| 6,755,842 | B2 | 6/2004 | Kanner et al. |
| 6,767,356 | B2 | 7/2004 | Kanner et al. |
| 6,780,197 | B2 | 8/2004 | Roe et al. |
| 7,056,325 | B1 * | 6/2006 | Makower et al. ............. 606/153 |
| 7,101,395 | B2 | 9/2006 | Tremulis et al. |
| 7,112,207 | B2 | 9/2006 | Allen et al. |
| 7,334,718 | B2 * | 2/2008 | McAlister et al. ......... 227/175.1 |
| 7,556,632 | B2 | 7/2009 | Zadno |
| 2001/0007077 | A1 | 7/2001 | Ginn et al. |
| 2001/0021855 | A1 | 9/2001 | Levinson |
| 2002/0013571 | A1 | 1/2002 | Goldfarb et al. |
| 2002/0072768 | A1 | 6/2002 | Ginn |
| 2002/0082641 | A1 | 6/2002 | Ginn et al. |
| 2002/0133193 | A1 | 9/2002 | Ginn et al. |
| 2002/0151921 | A1 | 10/2002 | Kanner |
| 2002/0156495 | A1 | 10/2002 | Brenneman et al. |
| 2002/0193808 | A1 | 12/2002 | Belef et al. |
| 2003/0078598 | A1 | 4/2003 | Ginn et al. |
| 2003/0097140 | A1 | 5/2003 | Kanner |
| 2003/0100920 | A1 | 5/2003 | Akin et al. |
| 2003/0109890 | A1 | 6/2003 | Kanner et al. |
| 2003/0158577 | A1 | 8/2003 | Ginn et al. |
| 2003/0158578 | A1 | 8/2003 | Pantages et al. |
| 2004/0002681 | A1 | 1/2004 | McGuckin, Jr. et al. |
| 2004/0010285 | A1 | 1/2004 | Carley et al. |
| 2004/0059375 | A1 | 3/2004 | Ginn et al. |
| 2004/0073236 | A1 | 4/2004 | Carley et al. |
| 2004/0073255 | A1 | 4/2004 | Ginn et al. |
| 2004/0153122 | A1 | 8/2004 | Palermo |
| 2004/0153123 | A1 | 8/2004 | Palermo et al. |
| 2004/0176798 | A1 | 9/2004 | Epstein et al. |
| 2004/0225301 | A1 | 11/2004 | Roop et al. |
| 2005/0021054 | A1 | 1/2005 | Ainsworth et al. |
| 2005/0090834 | A1 | 4/2005 | Chiang et al. |
| 2005/0090843 | A1 | 4/2005 | Bolduc |
| 2005/0131460 | A1 | 6/2005 | Gifford, III et al. |
| 2005/0187613 | A1 | 8/2005 | Bolduc et al. |
| 2006/0122647 | A1 | 6/2006 | Callaghan et al. |
| 2006/0151568 | A1 * | 7/2006 | Weller et al. ............. 227/175.1 |
| 2006/0200197 | A1 | 9/2006 | Brenzel et al. |
| 2006/0217744 | A1 * | 9/2006 | Bender et al. ............... 606/142 |
| 2006/0271089 | A1 | 11/2006 | Alejandro et al. |

FOREIGN PATENT DOCUMENTS

| | | |
|---|---|---|
| WO | WO-00/07640 | 2/2000 |
| WO | WO-00/56223 | 9/2000 |
| WO | WO-00/56227 | 9/2000 |
| WO | WO 2005/027753 | 3/2005 |
| WO | WO 2005/034763 | 4/2005 |

OTHER PUBLICATIONS

"Closure and Assisted-Compression Device Update", *Endovascular Today*, (Apr. 2004),22.

"Summary of Safety and Effectiveness Data (EVS (TM) Vascular Closure System)", (Nov. 3, 2004).

"The EVS(TM) Vascular Closure System by Angiolink", *Business Briefing: US Cardiology 2004*, (2004).

"VasoStasis (TM) Vascular Closure System 510(k) Notification", (Oct. 22, 2004).

* cited by examiner

APPARATUS AND METHOD FOR CLOSURE OF PATENT FORAMEN OVALE

FIELD OF THE INVENTION

The present invention relates generally to a system for closing a patent foramen ovale in heart tissue.

BACKGROUND

Figure 1:
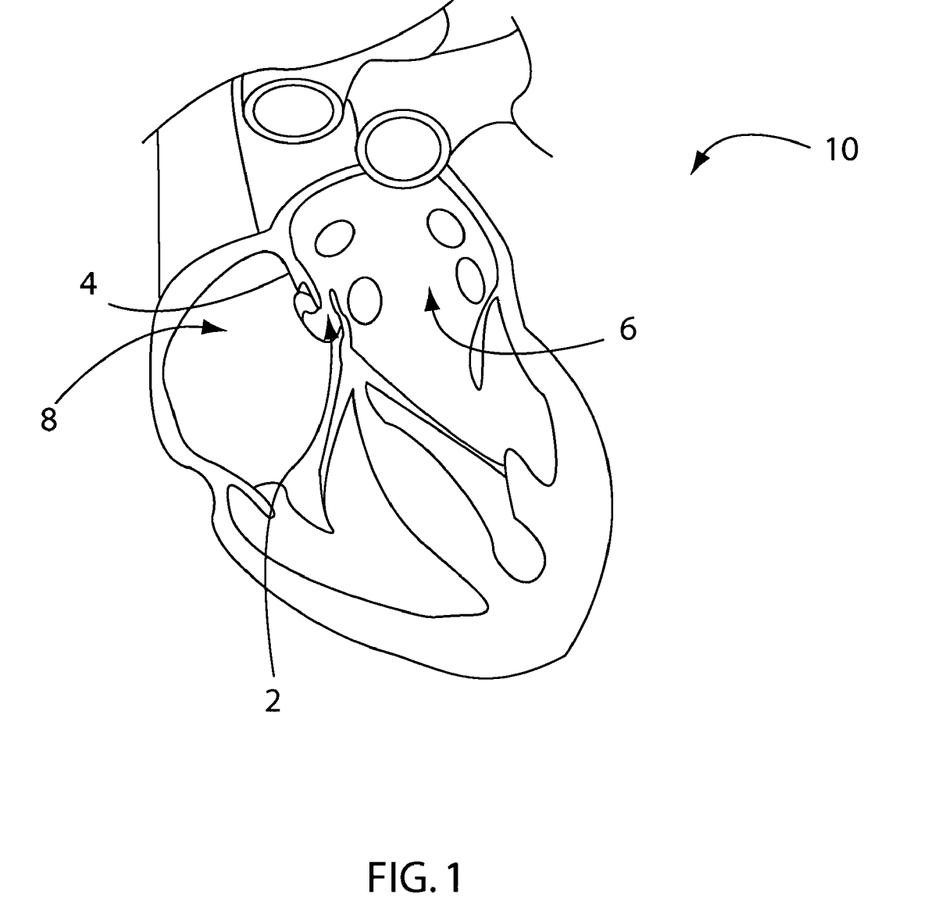
FIG. 1 is a cross-section view of a heart.

Referring to FIG. 1, a patent foramen ovale (PFO) 2 is a flap-like opening in the wall 4 between the left atrium 6 and the right atrium 8 of the heart 10. That opening typically closes at or shortly after birth. However, in an estimated 20-25% of people, the PFO 2 remains open into adulthood. The PFO 2 allows blood clots in the bloodstream to bypass the natural filtering mechanism of the lungs, which can lead to stroke. A person with a PFO 2 is generally asymptomatic, and generally does not know he or she has a PFO 2 until after a stroke. In addition, research suggests a correlation between PFO 2 and migraine, the mechanism of which is still unknown.

Currently, patients having a known PFO 2 are treated in one of two ways. The patient may be prescribed blood thinners such as coumadin, to reduce the risk of clot formation. However, this course of treatment requires lifelong dependence on that medication, which does nothing to close the opening between the atria. Alternately, a device may be placed through the PFO 2 and then unfurled like a tent on each side of the PFO 2. Such a device may include a material such as polyester stretched over a wire frame, or stuffed inside a wire mesh. However, such devices can expose a significant amount of metal to the bloodstream, which is considered undesirable.

BRIEF DESCRIPTION OF THE DRAWINGS

The use of the same reference symbols in different figures indicates similar or identical items.

DETAILED DESCRIPTION

Figure 2:
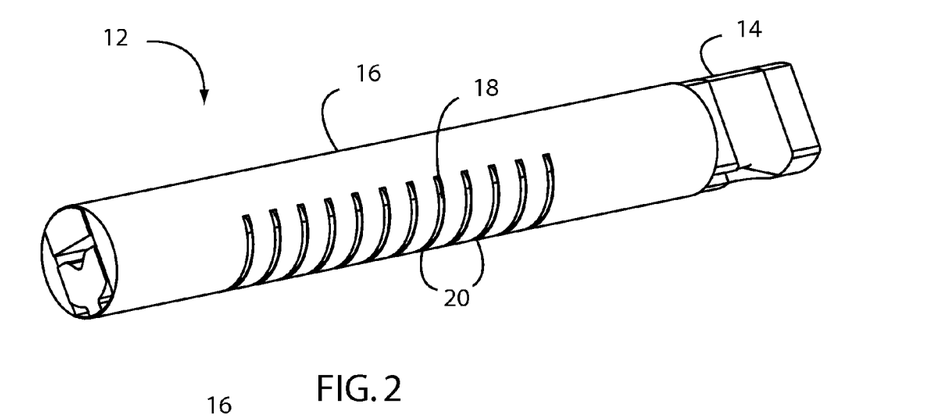
FIG. 2 is a perspective view of an exemplary connector applicator.

Referring to FIG. 2, a connector applicator 12 includes a driver 14 movable relative to a housing 16. The housing 16 may be substantially tubular. Alternately, the housing 16 may be shaped in any other suitable manner. The housing 16 is substantially rigid. Alternately, at least part of the housing 16 may be flexible. The housing 16 may be fabricated from any suitable material. A plurality of connectors 18 are held by the connector applicator 12.

Figure 3:
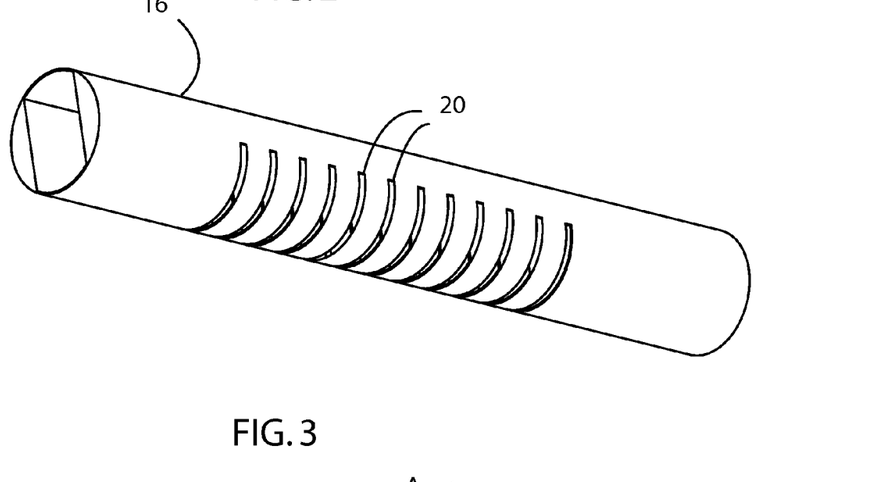
FIG. 3 is a perspective view of an exemplary housing that forms part of the connector applicator of FIG. 2.
Figures 4, 5:
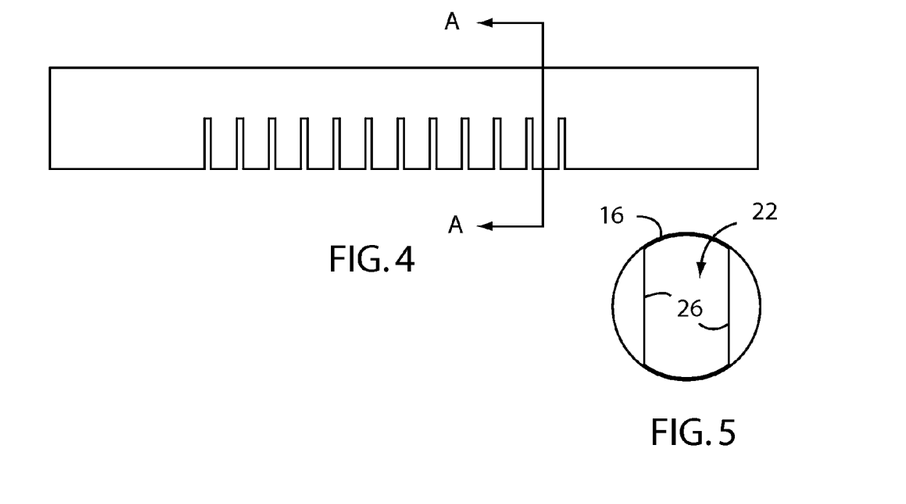
FIG. 4 is a side view of the housing of FIG. 3.
FIG. 5 is a cross-section view of the housing of FIG. 4 along the line A-A of FIG. 4.

Referring also to FIGS. 3-4, slots 20 may be defined in the housing 16. The slots 20 are aligned with the connectors 18 held by the connector applicator 12 in order to allow the connectors 18 to be deployed through those slots 20, as described in greater detail below. The slots 20 may extend far enough around the circumference of the housing 16 to allow the connectors 18 to splay before closing, where the connectors 18 are configured to splay. Each slot 20 is as least as wide as the corresponding connector 18 is thick, to allow the corresponding connector 18 to be deployed through that slot 20. Referring to FIG. 5, the housing 16 includes a lumen 22 therethrough. That lumen may be any suitable shape. As one example, the lumen 22 may include two straight, substantially-perpendicular sides opposite one another, and two arcuate sides opposite each other, where each arcuate side is a portion of the circumferential shell of the housing 16. As a result, two walls 26 may be located both proximally and distally to each slot 20, where each wall 26 may be a generally solid region between the straight side of the lumen 22 and the shell of the housing 16. Consequently, each slot 20 may be a bay-like area within the housing 16, where the walls 26 restrain the connector 18 that is located in the slot from moving substantially in the longitudinal direction during deployment.

Figure 6:
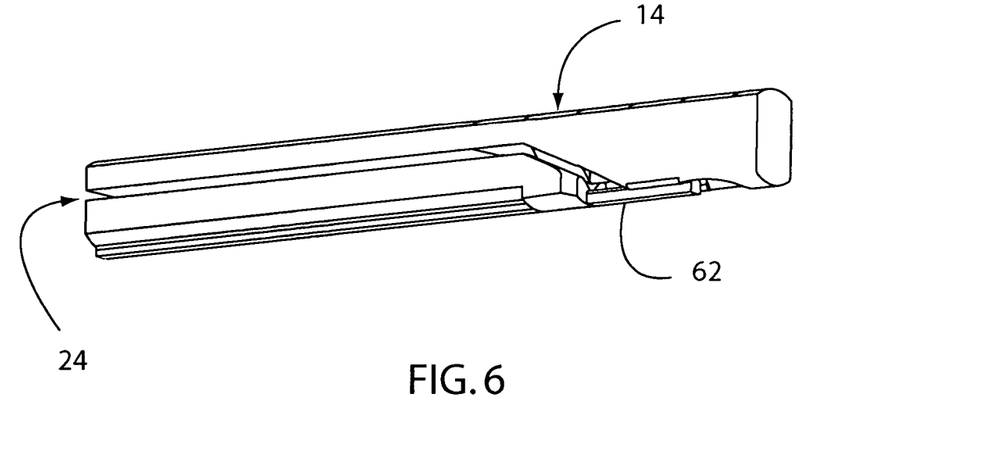
FIG. 6 is a perspective of an exemplary driver that forms part of the connector applicator of FIG. 2.
Figure 7:
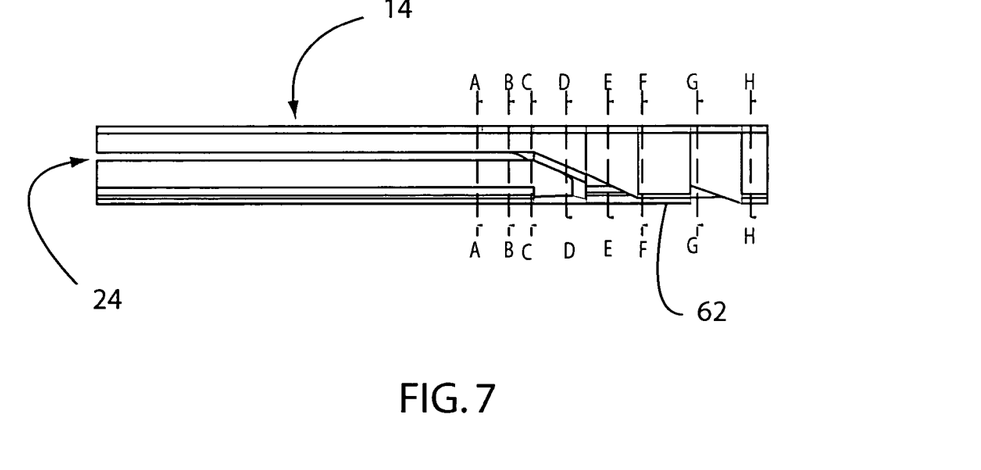
FIG. 7 is a side view of the driver of FIG. 6.

Referring to FIGS. 6-7, the driver 14 has a shape that varies in cross-section along at least part of its length. The driver 14 includes a generally longitudinal passage 24 defined therein. The longitudinal passage 24 may divide the driver 14 into two or more parts. That is, the driver 14 may include one or more physically-separate components. In such an embodiment, the different portions of the driver 14 can be driven by pulling them at the same rate with separate cables (one attached to each portion), a single cable attached to all of the portions, or any other suitable mechanism or mechanisms attached to one or all portions. Alternatively, the spaced-apart portions of the driver 14 can be joined together at the side to the right of the 'H' label in FIG. 7, such that the driver 14 could be driven by pulling a single cable or other mechanism attached to the driver 14. At least part of at least one connector 18 is positioned within the longitudinal passage 24. The driver 14 is shaped such that it is movable relative to at least one connector 18 to change the shape of that connector 18. Each connector 18 is held within a corresponding slot 20 in the housing 16 that maintains the connector 18 in substantially the same longitudinal position during the motion of the driver 14. As a result, as the driver 14 is moved relative to the connector 18, the cross-section of the driver 14 that engages the connector 18 changes, causing the connector 18 to change shape. FIGS. 8-15 show the cross-section of the longitudinal passage 24 at various points along the driver 14 identified in FIG. 7. These figures, and the effects of the changing cross-section on the connectors 18, are described in greater detail below. Optionally, at least part of the driver 14 may be coated with a biocompatible lubricant such as sodium stearate. Optionally, at least two connectors 18 may be connected by a backbone 19, referring to FIG. 19C. The backbone 19 may be flexible, rigid, or configured in any other suitable manner. The backbone can be made of the same material as the connectors 18, or of any other suitable material, such as suture or metal wire. Advantageously, all connectors 18 are interconnected by the backbone 19.

Figure 19:
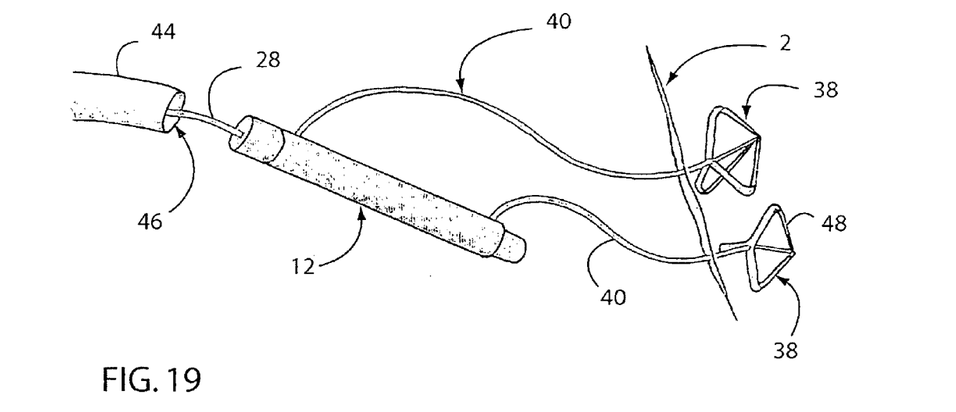
FIG. 19 is a perspective view of an exemplary step of closing a PFO.
Figure 19A:
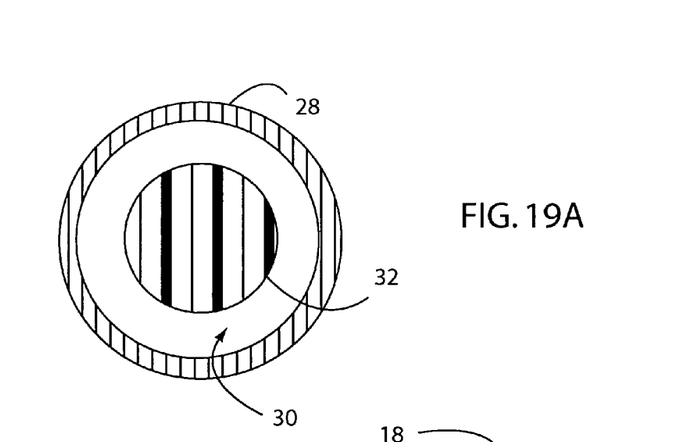
FIG. 19A is a cross-section view of an exemplary tube that is connected to the connector applicator of FIG. 2.

Referring also to FIGS. 19 and 19A, the connector applicator 12 may be connected to a tube 28 in any suitable manner. The tube 28 is advantageously flexible, and has a lumen 30 defined therein. A control wire 32 may be connected to the driver 14, and may extend through the lumen 30 of the tube 28. The control wire 32 may be connected to the driver 14 in any suitable manner. The application of tension to the control wire 32 causes the driver 14 to move along the lumen 22 of the housing 16 or move in any other suitable manner relative to the housing 16, as described in greater detail below. The control wire 32 may be connected to a handle (not shown) or other structure or mechanism outside the patient, to enable control of the driver 14.

Figure 19B:
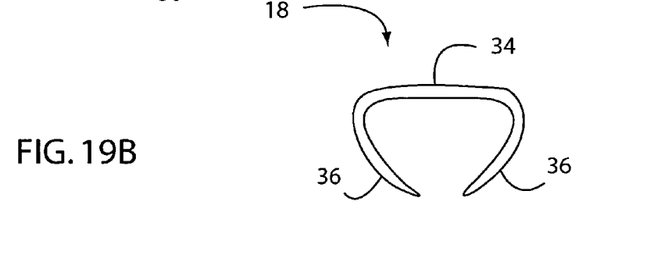
FIG. 19B is a front view of an exemplary connector used in conjunction with the connector applicator of FIG. 2.
Figure 19C:
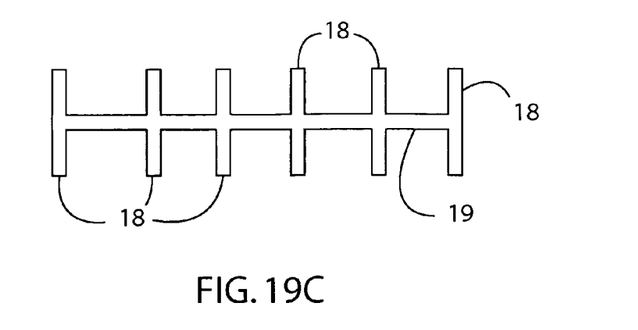
FIG. 19C is a top view of a number of connectors of FIG. 19B interconnected by an exemplary backbone.

The connectors 18 may be configured in any suitable manner. As one example, referring to FIG. 19B, at least one connector 18 may be a wire staple having a substantially straight base 34 connected at each end to a curved tine 36. The connector 18 may be sized, and the tines 36 curved, such that the curvature of each tine 36 is substantially the same as that of the housing 16 and such that the outer surface of each tine 36 is slightly closer to the longitudinal centerline of the housing 16 than the outer surface of the housing 16. Each connector 18 may be a staple, clip or any other suitable structure or mechanism. The connectors 18 may be all of a single or similar configuration. Alternately, at least one connector 18 may be shaped differently, fabricated from different materials, or otherwise configured differently than at least one other connector 18. As one example, at least one connector 18 may be substantially as disclosed in U.S. patent application Ser. No. 11/093,003, "Vascular Closure System," filed on Mar. 28, 2005, which is hereby incorporated by reference in its entirety. As another example, at least one connector may be substantially as disclosed in U.S. patent application Ser. No. 11/282,177, "Vascular Closure System Utilizing a Staple," filed on Nov. 4, 2005, which is hereby incorporated by reference in its entirety.

Figure 18:
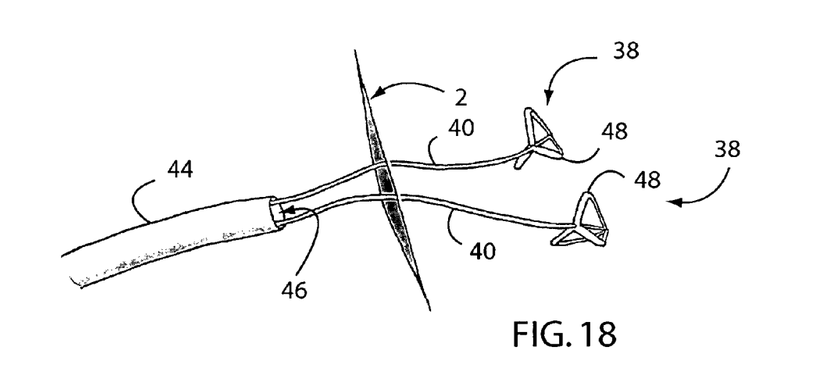
FIG. 18 is a perspective view of an exemplary step of closing a PFO.

Referring to FIG. 18, at least one anchor 38 may be utilized in conjunction with the connector applicator 12. Each anchor 38 is a mechanism movable from a first configuration having a first width to a second configuration having a second, larger width, then back to the first configuration. Each anchor 38 may be configured in any suitable manner. As one example, at least one anchor 38 may be a tubular structure having two or more slots defined therethrough, such that compression of the anchor causes the segments 48 of the anchor 38 between the slots to deform outward. At least one anchor 38 may have a blunt or soft distal end. Optionally, a soft tip fabricated from rubber, silicone or other soft biocompatible material may be connected to the distal end of at least one anchor 38.

Each anchor 38 may be connected to a corresponding tether 40. Where the corresponding anchor 38 is originally in a substantially tubular state and/or is configured to have a lumen therethrough, the tether 40 may extend into that lumen and connect to the distal end of the anchor 38. The tether 40 may be tensioned in order to compress the corresponding anchor 38 and cause segments 48 thereof to expand outward. At least one anchor 38 may be elastically deformable. If so, the anchor 38 is in the first configuration until the tether 40 is tensioned to deform the anchor 38 to the second configuration, and the anchor 38 remains in the second configuration until the tether 40 is released Alternately, at least one anchor 38 may be superelastically deformable. For example, such an anchor 38 may be fabricated from nickel-titanium alloy. Alternately, at least one anchor 38 may be plastically deformable. Such an anchor 38 may be substantially as disclosed in U.S. patent application Ser. No. 11/093,003. The housing 16 of the connector applicator 12 may include at least two apertures defined therein, where at least one tether 40 passes through an aperture different from at least one other tether 40. The passage of tethers 40 through different apertures allows the connector applicator 12 to be properly located relative to the PFO 2, as described in greater detail below. Optionally, the tethers 40 may extend through the tube 28 as well.

Operation

Figure 16:
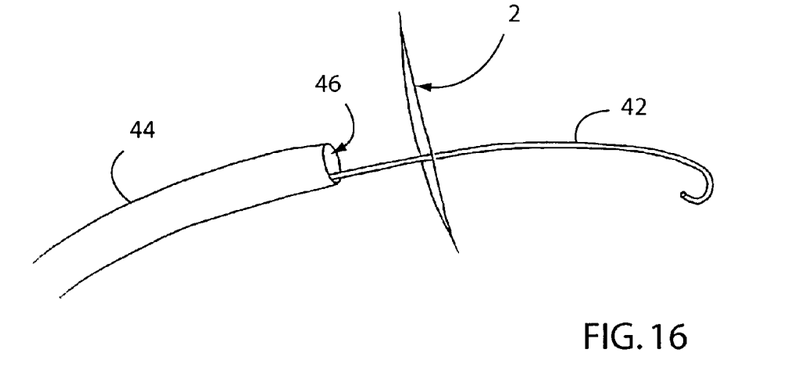
FIG. 16 is a perspective view of an exemplary step of closing a PFO.

Referring to FIG. 16, a conventional guidewire 42 is inserted percutaneously into the patient and advanced through the vasculature to the PFO 2. Any suitable guidewire 42 may be used. Insertion of the guidewire into the patient may be through conventional femoral artery or radial artery access, or through any other blood vessel that allows the guidewire 42 to be advanced through the vasculature to the PFO 2. After the guidewire 42 reaches the PFO 2, it is advanced completely through the PFO 2. The advancement of the guidewire 42 advantageously may be performed with the assistance of a fluoroscope or other imaging device that indicates the position of the guidewire 42 in the patient. The use of such an imaging device in conjunction with a guidewire 42 is standard in the art.

Figure 17:
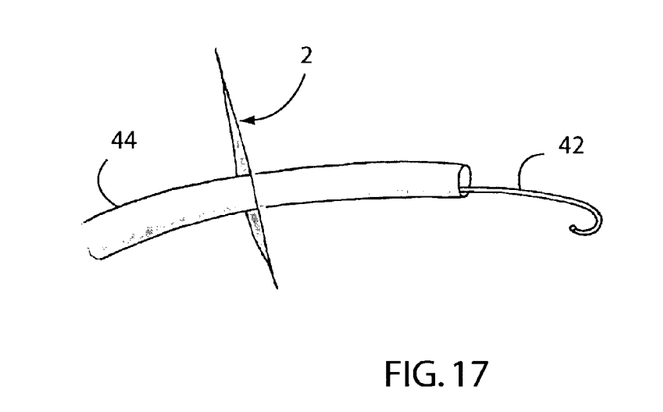
FIG. 17 is a perspective view of an exemplary step of closing a PFO.

A conventional sheath 44 is then advanced through the vasculature, along and over the guidewire 42. The sheath 44 is substantially tubular, and includes a lumen 46 defined therein. The sheath 44 is advantageously flexible. Any suitable sheath 44 may be used. The use of a sheath 44 in conjunction with a guidewire 42 is standard in the art. Referring also to FIG. 17, the sheath 44 continues to be advanced along and over the guidewire 42 until the distal end of the sheath 44 passes through the PFO 2. Alternately, the distal end of the sheath 44 may be advanced to a point where it is adjacent to the PFO 2 without passing through the PFO 2.

Next, referring to FIG. 18, the guidewire 42 is removed from the sheath 44, leaving the lumen 46 of the sheath 44 clear. Alternately, the guidewire 42 may remain in place, particularly if the sheath 44 includes more than one lumen. The anchors 38 are then delivered through the lumen 46 of the sheath 44 to the side of the PFO 2 opposite to the side of the PFO 2 from which the sheath 44 approached. The anchors 38 are then expanded, simultaneously or at different times, in any suitable manner. Alternatively, a single anchor 38, or more than two anchors 38, can be used. As one example, at least one anchor 38 may be a tubular structure having two or more slots defined therethrough, such that compression of the anchor causes the segments 48 of the anchor 38 between the slots to deform outward. The corresponding tether 40 extends through the tubular anchor 38 and is attached to the distal end of that anchor 38. A flexible tube (not shown) or similar structure may be connected to the proximal end of the anchor 38, and the tether 40 may extend through that tube. To expand the anchor 38, the tether 40 is pulled in the proximal direction, tensioning the tether 40 and imparting a force in the proximal direction on the anchor 38. The tube connected to the proximal end of the anchor 38 prevents the anchor 38 from moving substantially in the proximal direction, and as a result the force exerted on the anchor 38 by the tether 40 exerts a compressive force on the anchor 38. This compressive force causes the segments 48 of the anchor 38 between the slots to deform outward, expanding the anchor to its second, expanded configuration. As another example, at least one anchor 38 may be expanded in a manner substantially as disclosed in U.S. patent application Ser. No. 11/093,003. Any other suitable method or structure may be used to expand the anchors 38, if desired. Advantageously, two anchors 38 are delivered through the sheath 44 across the PFO 2, but more than two anchors 38 or only one anchor 38 may be used.

Figure 20:
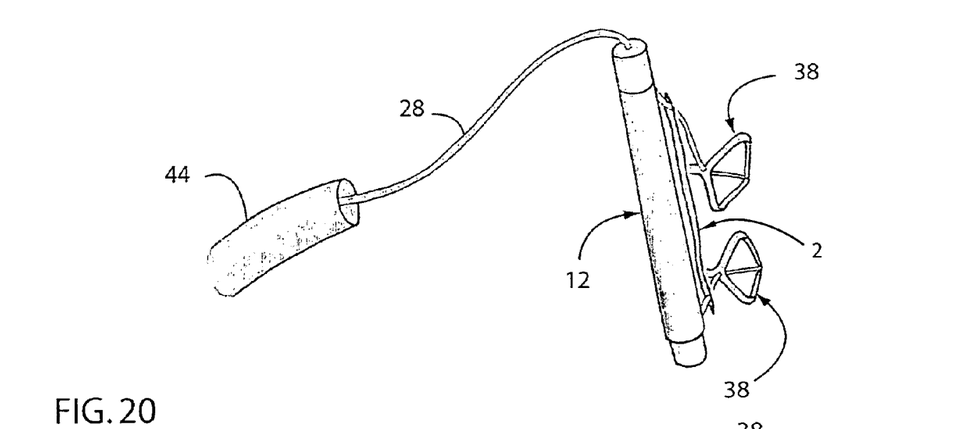
FIG. 20 is a perspective view of an exemplary step of closing a PFO.

Next, the sheath 44 is retracted back across the PFO 2, such that the expanded anchors 38 are on one side of the PFO 2 and the sheath 44 is on the other side of the PFO 2. Referring to FIG. 19, the connector applicator 12 is then delivered through the lumen 46 of the sheath 44 to the side of the PFO 2 opposite from the side on which the expanded anchors 38 are located. The tube 28 is connected to the connector applicator 12, and extends along the lumen 46 of the sheath 44 out of the patient, or to a location where the tube 28 can be manipulated. At least one tether 40 passes through an aperture in the housing 16 of the connector applicator 12 that is different from the aperture through which at least one other tether 40 passes, as described above. Referring to FIG. 20, the tethers 40 are then pulled proximally, tensioning them. This motion of the tethers 40 pulls the anchors 38 and the connector applicator 12. As the anchors 38 move toward the PFO 2, they engage heart tissue adjacent to the PFO 2. In the expanded state, the anchors 38 are too large to pass through the PFO 2. Thus, when the anchors 38 engage the heart tissue adjacent to the PFO 2, and the tethers 40 continue to be pulled proximally, the anchors 38 do not move further, and the connector applicator 12 moves toward the PFO 2. Alternately, the connector applicator 12 may engage the heart tissue adjacent to the PFO 2 first.

Figure 21:
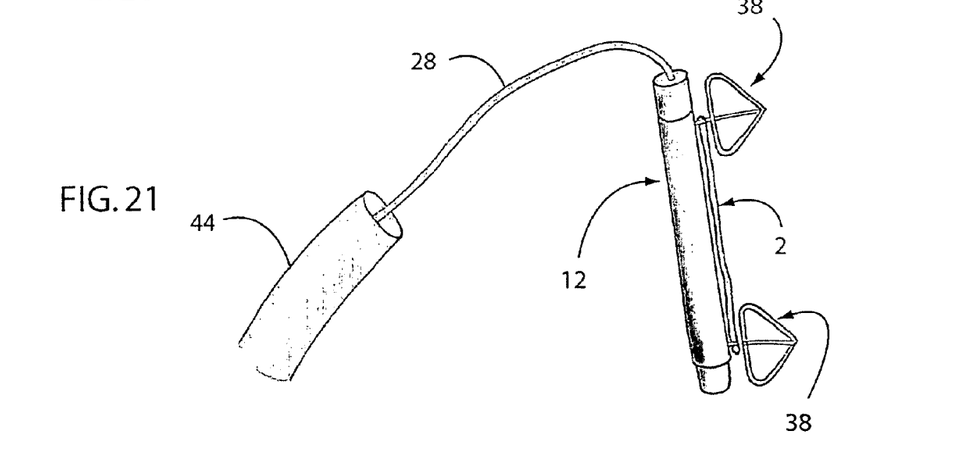
FIG. 21 is a perspective view of an exemplary step of closing a PFO.

Referring also to FIG. 21, the connector applicator 12 and the anchors 38 eventually both contact the heart tissue adjacent to the PFO 2, such that they cannot be pulled together substantially closer to one another. At that time, the length of tether 40 between the connector applicator 12 and each anchor 38 is relatively short. The apertures in the housing 16 that are spaced furthest from one another are spaced apart a distance at least as far as the expected length of the PFO 2, and advantageously further than the expected length of the PFO 2. Thus, as the tethers 40 are retracted and the connector applicator 12 and anchors 38 move closer together, the PFO 2 is tensioned as well. That is, the ends of the PFO 2 are stretched further apart, such that the tissue on the edges of the PFO 2 is drawn closer together. The tensioned PFO 2 thus may be more linear, and may be narrower, than in its original shape. Before the procedure, the device can be adjusted to accommodate the expected length of the PFO 2. This can be accomplished by adjusting the positions where the anchor tethers 40 enter and/or are held by the connector applicator 12, such that the anchor tethers 40 are spaced apart a distance slightly larger than the length of the PFO 2. This spacing will tension the PFO 2 as described above.

At this point, the connector applicator 12 is substantially aligned with the PFO 2, and is adjacent to the PFO 2. The connector applicator 12 may be characterized as being registered to the PFO 2 in this position. At this time, the driver 14 is actuated to begin deployment of the connectors 18. The driver 14 may be actuated in any suitable manner. As one example, referring also to FIG. 19A, a control wire 32 is attached to the driver 14, and the control wire 32 is pulled proximally, causing the driver 14 to slide along the lumen 22 of the housing 16. However, the driver 14 may be actuated in any other suitable manner.

Figure 8:
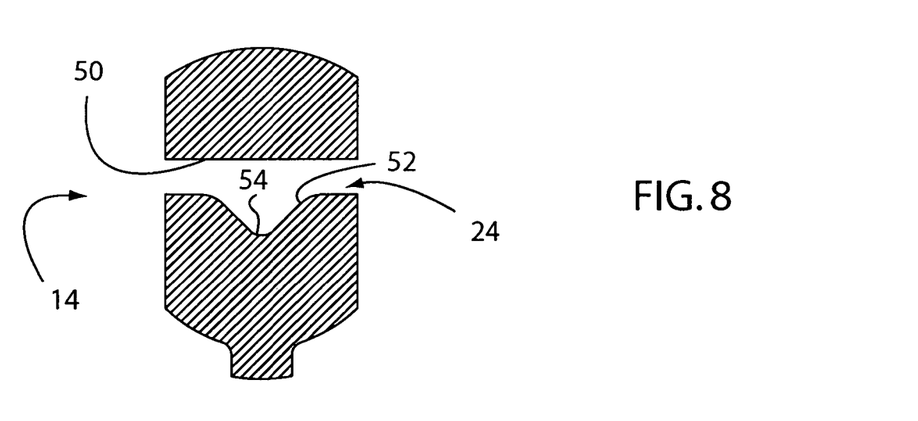
FIG. 8 is a cross-section view of the driver of FIG. 6 along the line A-A of FIG. 6.

Advantageously, the driver 14 sequentially deforms and deploys the connectors 18, such that different connectors 18 may be in different stages of deformation and/or deployment at any particular moment. For clarity, the deformation and deployment of a single connector 18 is described, and this deformation and deployment may be generalized to all of the connectors 18. Referring to FIG. 7, a side view of the driver 14 is shown. The driver 14 moves in the left direction, this being no limitation on the orientation of the connector applicator 12 in use or the orientation of the driver 14 in the connector applicator 12. Connectors that have not yet been deformed are positioned at or to the left of cross-section line A-A, with the base 34 of the connector positioned within the passage 24 of the driver. Referring to FIG. 8, at the cross-section line A-A, the passage 24 is open laterally, to allow the straight base of the connector 18 to be held therein. The upper surface 50 of the passage 24 may be substantially flat, such that the base 34 of the connector 18 may contact that upper surface 50. Alternately, the upper surface 50 may be shaped in any other suitable manner. The lower surface 52 of the passage 24 may be flat in proximity to each lateral edge of the passage 24, and include a depression 54 at a location substantially in the center of the lower surface 52. The depression 54 may be a concave, curved surface, or may be shaped in any other suitable manner.

Figure 9:
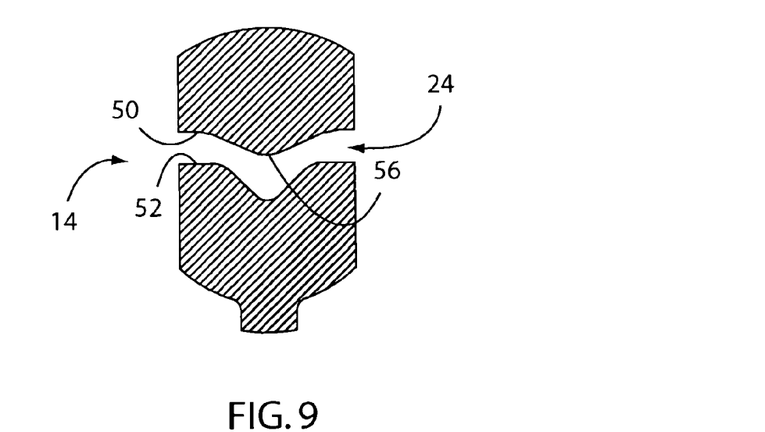
FIG. 9 is a cross-section view of the driver of FIG. 6 along the line B-B of FIG. 6.
Figure 9A:
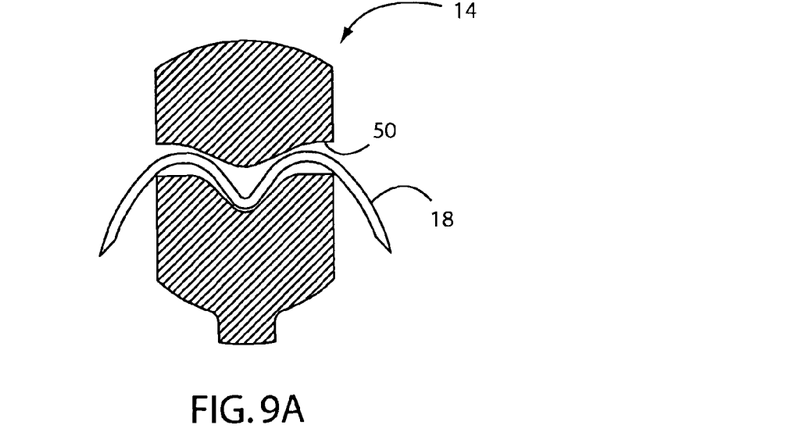
FIG. 9A is the cross-section view of FIG. 9, showing a connector in a splayed configuration.

As the driver 14 is moved to the left, the connector 18 is held in substantially the same longitudinal position. Referring to FIG. 7, the cross-section of the driver 14, and of the passage 24, change between cross-section line A-A and cross-section line H-H. Thus, the connector 18 encounters the changes in the shape of the driver 14 and passage 24 as it is held in one place and the driver 14 is moved relative to it. As a result, the cross-section of the driver 14 and passage 24 can be shaped along a length of the driver 14 to produce a sequence of desired effects on the connector 18 as the driver 14 is moved relative to the connector 18. Referring also to FIG. 9, as the driver 14 is moved left, the connector 18 encounters the portion of the driver 14 at cross-section line B-B. At this cross-section B-B, a projection 56 extends downward at a location substantially in the center of the upper surface 50. The projection 56 may be a convex, curved surface, or may be shaped in any other suitable manner. The lower surface 52 of the passage 24 at cross-section line B-B may be shaped in substantially the same manner as at cross-section A-A. Referring also to FIG. 9A, when the portion of the driver 14 at cross-section B-B encounters the connector 18, the projection 56 from the upper surface 50 of the passage 24 begins to bend the center of the base 34 of the connector 18 downward. Consequently, the ends of the tines 36 begin to move outward, apart from one another. This deformation of the connector 18 may be referred to as "splaying". As the connector 18 begins to splay, at least a portion of at least one tine 36 may move out of the housing 16 through the corresponding slot 20 in the housing 16. As a result, the ends of the tines 36 may move apart from one another a distance greater than the diameter of the housing 16. During splaying of the connector 18, the tines 36 themselves may remain substantially undeformed; rather, the base 34 of the connector 18 deforms to cause the ends of the tines 36 to move apart from one another. Alternately, at least one tine 36 may deform at some point during splaying of the connector 18. Where the connector 18 is made from a plastically-deformable material such as stainless steel, the connector 18 deforms plastically as it splays from its initial configuration to the splayed configuration. Plastic deformation is deformation that remains after the load that caused it is removed, or that would remain if the load were removed. Alternately, the connector 18 is elastically or superelastically deformable from its initial configuration to the splayed configuration.

Figure 10:
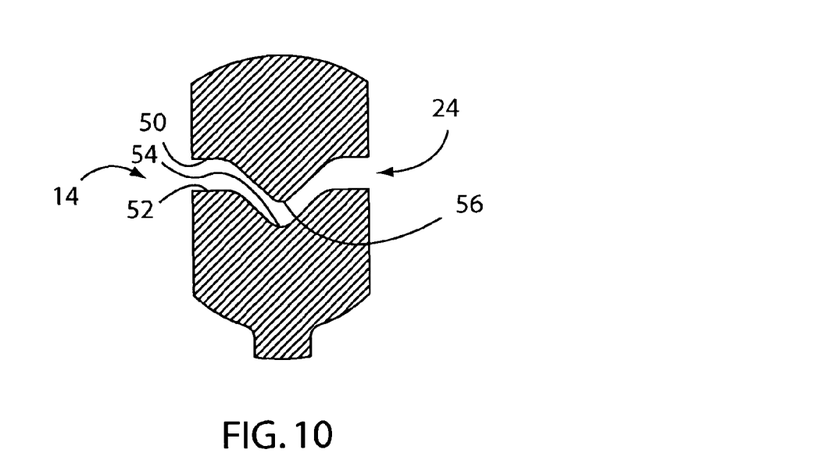
FIG. 10 is a cross-section view of the driver of FIG. 6 along the line C-C of FIG. 6.

The driver 14 continues its motion to the left. Referring to FIG. 10, the connector 18 next encounters the portion of the driver 14 at cross-section line C-C. At this cross-section C-C, a projection 56 extends downward to a greater extent than at cross-section line B-B. The lower surface 52 of the passage 24 at cross-section line C-C may be shaped in substantially the same manner as at cross-section B-B. The shape of the projection 56 may be substantially the same as the depression 54 in the lower surface 52, and the space between the depression 54 and the surface 53 may be substantially the same as the thickness of the base 34 of the connector 18. The enlargement of the projection 56 in the downward direction causes the base 34 to bend to a greater degree than it did at cross-section B-B, causing the connector 18 to splay further outward. At cross-section line C-C, the connector 18 has completed splaying, such that the distal ends of the tines 36 are at their furthest point from each other. The tines 36 extend outward from the housing 16 through the corresponding slot 20.

Figure 11:
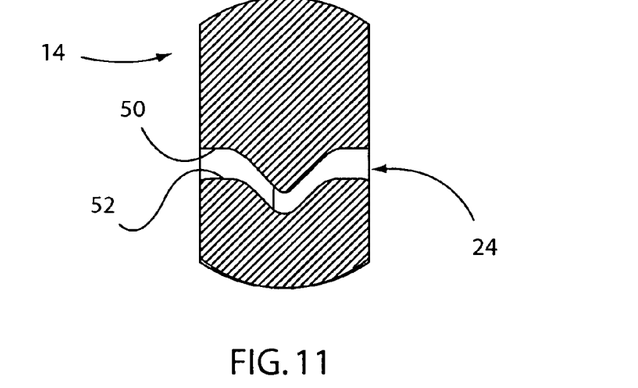
FIG. 11 is a cross-section view of the driver of FIG. 6 along the line D-D of FIG. 6.
Figure 22:
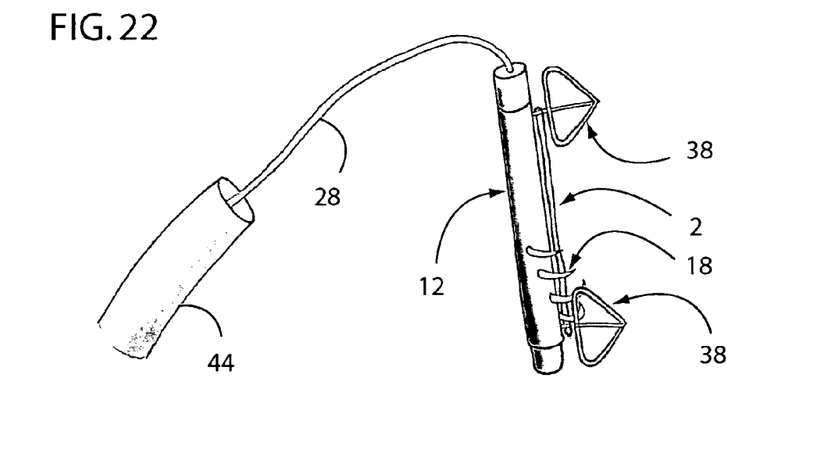
FIG. 22 is a perspective view of an exemplary step of closing a PFO.

Referring also to FIG. 11, as the driver 14 is moved left, the connector 18 encounters the portion of the driver 14 at cross-section line D-D. The upper surface 50 and the lower surface 52 are shaped substantially as at cross-section line C-C. However, both the upper surface 50 and the lower surface 52 are located below their positions at cross-section line C-C, because the passage 24 is sloped downward between cross-section line C-C and cross-section line D-D. The term "below" and other related terms such as "down" or "downward" are used solely for convenience, and refer to the orientation of the figures on the printed page; they do not and cannot limit the orientation or usage of the connector applicator 12. The passage 24 may be sloped in a linear manner, in a curved manner, or in any other suitable manner. The slope of the passage 24 pushes the connector 18 downward as the driver 14 moves left past the connector 18. Referring also to FIG. 22, as the connector 18 is pushed downward, the ends of the tines 36 engage heart tissue adjacent the PFO 2. Advantageously, the PFO 2 is located between the tines 36. The splayed configuration of the connector 18 allows capture of heart tissue across a width greater than that of the housing 16, and maximizes the amount of tissue that can be grasped between the tines 36.

Figure 12:
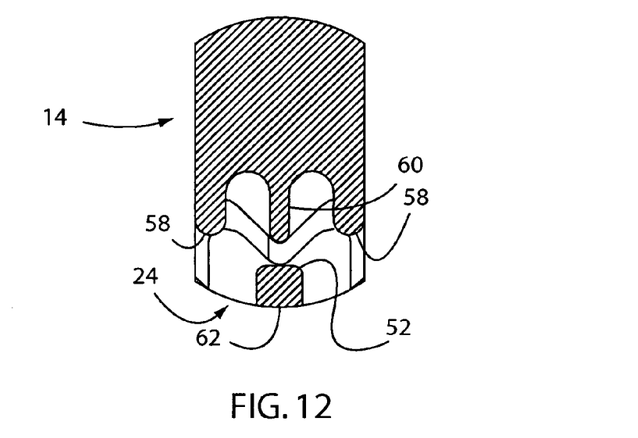
FIG. 12 is a cross-section view of the driver of FIG. 6 along the line E-E of FIG. 6.
Figure 12A:
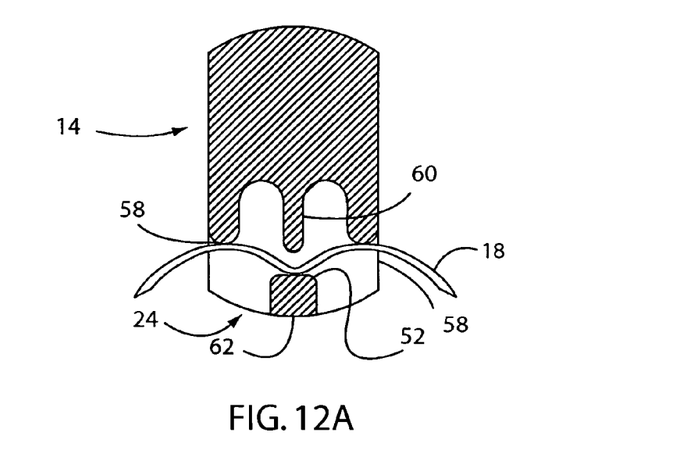
FIG. 12A is the cross-section view of FIG. 12, showing a connector beginning to close.

Referring also to FIG. 12, as the driver 14 is moved left, the connector 18 encounters the portion of the driver 14 at cross-section line E-E. The passage 24 continues to slope downward across at least part of the distance between cross-section line D-D and cross-section line E-E, pushing the connector 18 further downward and further into heart tissue in proximity to the PFO 2. At cross-section line E-E, the driver 14 is shaped to begin to close the connector 18. The lower surface 52 now extends across only a portion of the lateral width of the driver 14, providing room for the tines 36 to move inward. The lower surface 52 may be substantially centered laterally. Alternately, the lower surface 52 may be configured in any other suitable manner. Referring also to FIGS. 6-7, at this cross-section line E-E, the lower surface 52 of the passage 24 may be characterized as the upper surface of an anvil 62 formed in the driver 14. The upper surface 50 now is shaped to have two downward-extending projections 58, one at or in proximity to each lateral edge of the passage 24. Between the projections 58, the upper surface 50 may extend upward. Advantageously, the upper surface 50 includes a center projection 60 substantially centered between the lateral edges of the passage 24, and extending downward lower than the projections 58. Alternately, the center projection 60 is located differently, or extends downward a different length. Alternately, the upper surface 50 is configured in any other suitable manner. As the connector 18 encounters the portion of the driver 14 at cross-section line E-E, the projections 58 begin to deform the tines 36 about the lower surface 52. The center projection 60 holds the base 34 of the connector 18 between itself and the lower surface 52. The lower surface 52 prevents downward motion of the connector 18 as a whole, such that the downward force exerted on the splayed tines 36 by the projections 58 causes those tines 36 to rotate about the lower surface 52 and begin to close the connector 18. As the connector 18 closes, the tines 36 move closer to one another, compressing tissue between them. FIG. 12A shows the connector 18 beginning to close.

Figure 13:
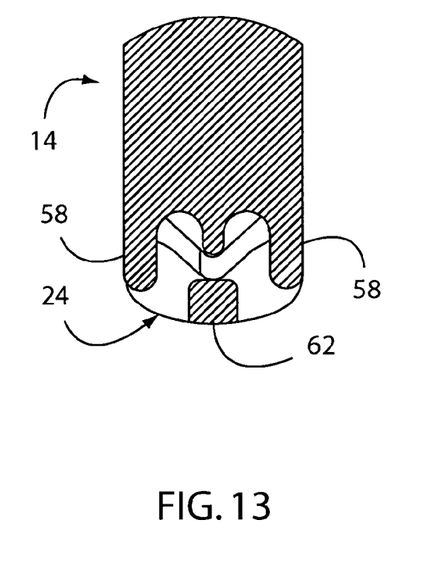
FIG. 13 is a cross-section view of the driver of FIG. 6 along the line F-F of FIG. 6.
Figure 13A:
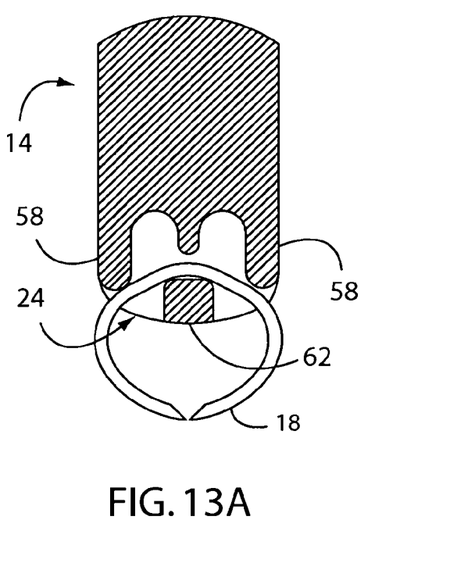
FIG. 13A is the cross-section view of FIG. 13, showing a connector in a closed configuration.

Referring also to FIG. 13, as the driver 14 is moved left, the connector 18 encounters the portion of the driver 14 at cross-section line F-F. The lower surface 52 of the passage 24 at cross-section line F-F may be substantially the same as at cross-section line E-E. At cross-section line F-F, the connector 18 is closed completely, and the lower surface 52 may be configured substantially as at cross-section line E-E to facilitate its use in closing the connector 18. Alternately, the lower surface 52 may be configured in any other suitable manner. The projections 58 extend downward further than at cross-section line E-E, and may extend to a location below the lower surface 52. The projections 58 increase their downward length from cross-section line E-E to cross-section line F-F, thereby continuing to exert a downward force on the connector 18. The connector 18 continues to deform about the lower surface 52 as a result, to a configuration such as shown in FIG. 13A. The tines 36 may stop their motion about the lower surface 52 before encountering each other when the connector 18 has reached the closed position, such as shown in FIG. 13A. Alternately, the tines 36 may pass one another before the connector 18 reaches the closed position. The center projection 60 continues to provide stability to the connector 18 as it deforms to the closed position.

Figure 14:
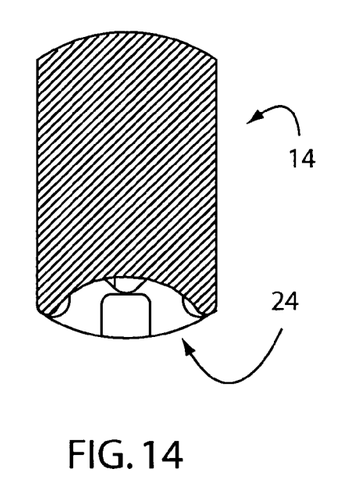
FIG. 14 is a cross-section view of the driver of FIG. 6 along the line G-G of FIG. 6.
Figure 15:
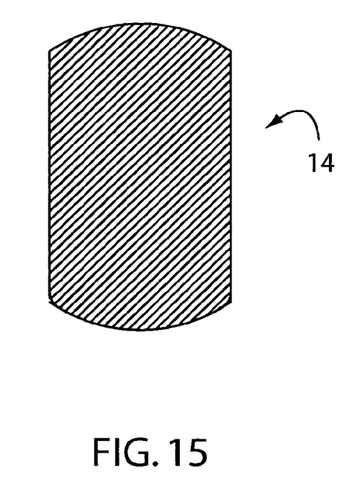
FIG. 15 is a cross-section view of the driver of FIG. 6 along the line H-H of FIG. 6.

Referring also to FIG. 14, as the driver 14 is moved left, the connector 18 encounters the portion of the driver 14 at cross-section line G-G. At cross-section line G-G, the passage 24 opens up, such that the lower surface 52 is no longer present.

That is, the anvil 62 has ended before the cross-section line G-G of the driver 14. Thus, the connector 18 is no longer restrained from moving completely out of the housing 16 through the corresponding slot 20. That is, the connector 18 has been released. The upper surface 50 may include projections 58 at its lateral edges to push the closed connector 18 out of the slot 20. Alternately, the force holding the closed connector 18 to tissue is greater than any frictional force holding the connector 18 to the connector applicator 12, such that the connector 18 is released from the connector applicator 12 at a later time when the connector applicator 12 is moved away from the PFO 2. Finally, as the driver 14 is moved left, referring also to FIG. 15, the passage 24 is no longer present in the driver 14 at cross-section line H-H. This transition in the shape of the driver 14 can act to eject the connector if it has not already moved out of the slot 20. Between cross-section line G-G and cross-section line H-H, the passage 24 extends downward, whether linearly, in a curved manner, or any other suitable manner. This downward extension of the passage 24 before the passage 24 disappears completely ejects the closed connector 18 from the housing 16 through the corresponding slot 20, because no space remains in the lumen 22 of the housing 16 to receive the base 34 of the connector 18.

Referring also to FIGS. 19A and 22, as the driver 14 is moved relative to the housing 16 by actuation of the control wire 32, the connectors 18 are deployed sequentially. As a result, different connectors 18 may be in different states of deployment simultaneously. For example, one or more connectors 18 may be moving toward or in the splayed configuration at the same time that one or more connectors 18 may be moving toward the closed configuration. The sequential splaying and closing of the connectors 18 results from the configuration of the driver 14 and the motion of the driver 14 relative to the connectors 18. Alternately, the driver 14 is configured and moved such that the connectors 18 are deployed substantially simultaneously, rather than sequentially.

Figure 23:
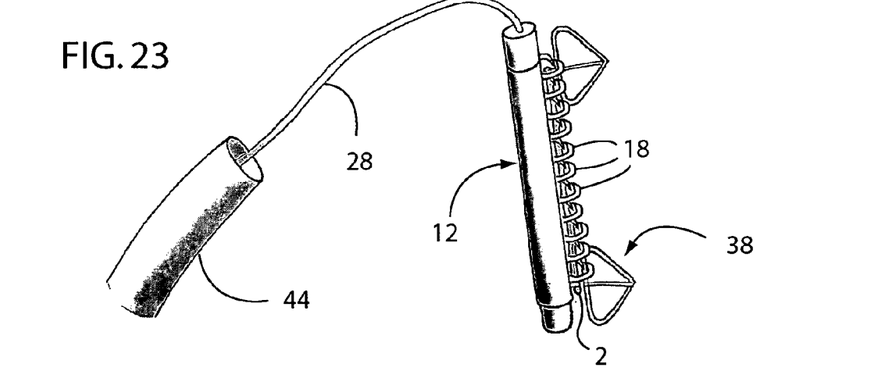
FIG. 23 is a perspective view of an exemplary step of closing a PFO.

Referring also to FIG. 23, after the driver 14 has completed its travel, the connectors 18 have all been deployed. The connectors 18 are in the closed position, straddling the PFO 2. The PFO 2 is now closed. Advantageously, each connector 18 is spaced substantially 1 mm apart from the neighboring connector 18 or connectors 18. Optionally, at least two connectors 18 are interconnected by a backbone 19, as described above. Alternatively, groups of connectors 18 can be joined together with multiple backbones 19. As an example, twelve connectors 18 can be joined together with four backbones 19, forming four groups of three connectors 18 each. The backbone 19 acts to hold the connectors 18 together, and may provide added stability and support for a connector 18 that may engage heart tissue with less force than other connectors 18. The connectors 18 are sized to minimize the amount of metal that is in contact with the bloodstream. Of course, the connectors 18 may be fabricated from a nonmetallic material. Similarly, where the backbone 19 is metallic, it is fabricated to be thin, in order to minimize the amount of metal in contact with the bloodstream. Alternately, the backbone 19 may be fabricated from a nonmetallic material. For example, the backbone 19 may be one or more strands of polyethylene.

Figure 24:
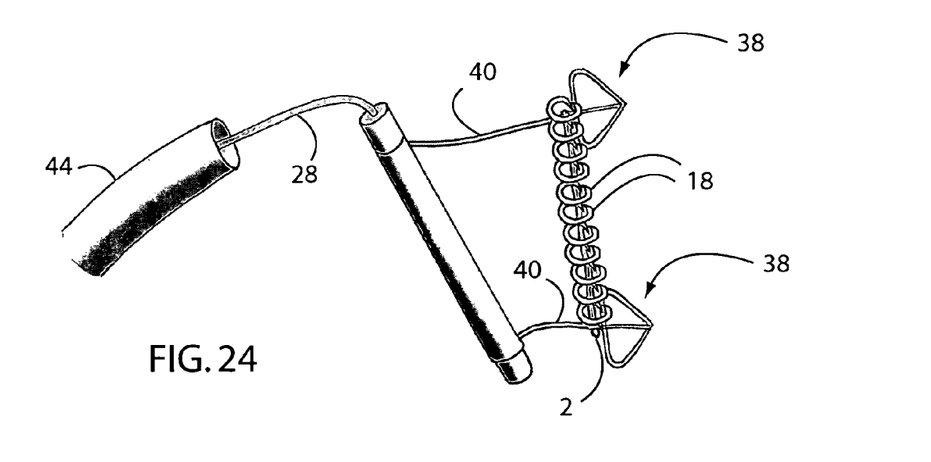
FIG. 24 is a perspective view of an exemplary step of closing a PFO.
Figure 25:
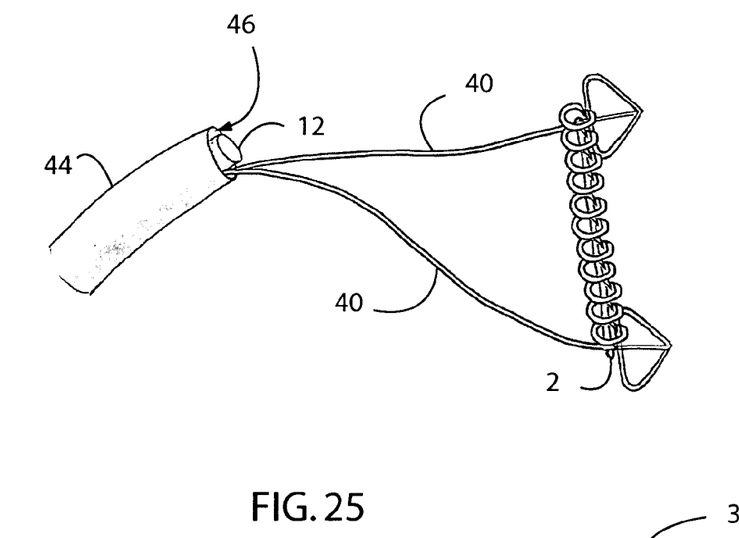
FIG. 25 is a perspective view of an exemplary step of closing a PFO.

Referring also to FIG. 24, after the connectors 18 have all been deployed, the connector applicator 12 is allowed to move away from the closed PFO 2. This may be accomplished by releasing tension on the tethers 40 and retracting the tube 28 attached to the connector applicator 12. By releasing tension on the tethers 40, the connector applicator 12 can be moved away from the anchors 38. Alternately, the connector applicator 12 may be moved away from the closed PFO 2 in any other suitable manner. Referring also to FIG. 25, the connector applicator 12 is then pulled substantially into the lumen 46 of the sheath 44, such as by continuing to retract the tube 28 attached to the connector applicator 12. The connector applicator 12 may remain substantially at the distal end of the lumen 46 of the sheath 44, may be removed completely from the sheath 44, or may be moved to any other suitable location within the lumen 46 of the sheath 44.

Figure 26:
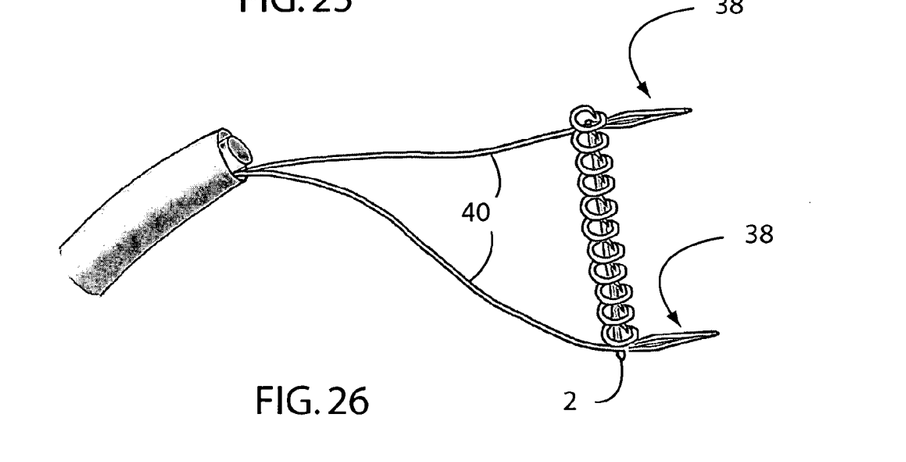
FIG. 26 is a perspective view of an exemplary step of closing a PFO.

Referring also to FIG. 26, the anchors 38 are collapsed from the second, expanded configuration back to the first, narrower configuration. The anchors 38 may be collapsed simultaneously, or at different times. This collapse may be performed in a manner opposite to which the anchors 38 were previously expanded. For example, the tension applied to at least one tether 40 may be released, allowing the corresponding anchors 38 to collapse back to the first, narrower configuration. Alternately, at least one tether 40 may be configured to allow transmission of compressive force. If so, each such tether 40 may be advanced distally, while a flexible tube or other structure connected to the proximal end of the corresponding anchor 38 holds the proximal end of the corresponding anchor 38 in place. As a result, the force exerted on the anchor 38 by the tether 40 exerts a tensile force on the anchor 38. This tensile force causes the segments 48 of the anchor 38 between the slots to deform inward, collapsing the anchor 38 to its second, expanded configuration. This method of collapsing the anchor 38 may be advantageous where the anchor 38 is plastically deformable, rather than elastically deformable.

Figure 27:
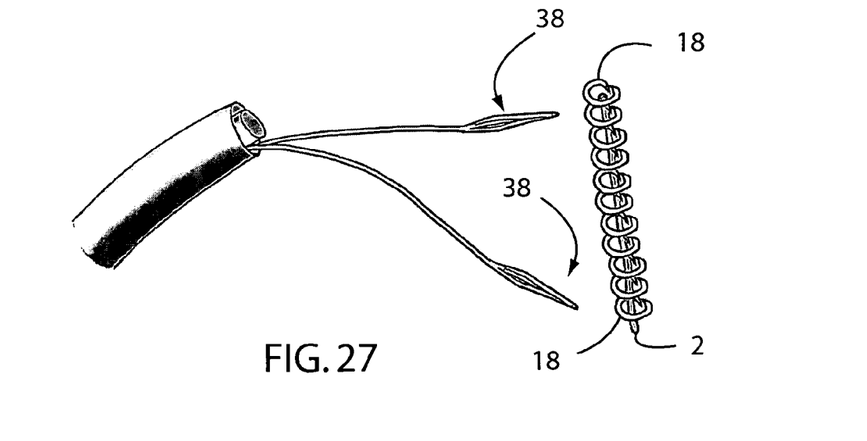
FIG. 27 is a perspective view of an exemplary step of closing a PFO.

Referring also to FIG. 27, the anchors 38 are then pulled through the closed PFO 2, such as by retracting the tethers 40. In the collapsed configuration, each anchor 38 is small enough to pass through the space between an end of the PFO 2 and the closest connector 18 and/or through the space between adjacent connectors 18. The anchors 38 are then pulled into the lumen 46 of the sheath 44, such as by continuing to retract the tethers 40. The anchors 38 may remain substantially at the distal end of the lumen 46 of the sheath 44, may be removed completely from the sheath 44, or may be moved to any other suitable location within the lumen 46 of the sheath 44. The sheath 44 is then removed from the patient, and the procedure is complete. Alternatively, one or more of the anchors 38 can be left in the PFO 2 as an implant. In such a case, the anchors 38 would assist in the closure of the PFO 2. The connectors 18 would engage the anchors 38 when they are formed. The anchors 38 would then be released from the connector applicator 12, leaving the connectors 18 and the anchors 38 in the PFO 2. This method may be advantageous where the anchors 38 include material that would help close the PFO 2. The vascular access incision made in the patient for insertion of the sheath 44 is closed in any suitable manner, such as by utilizing a device and method substantially as disclosed in U.S. patent application Ser. No. 11/093,003.

While the invention has been described in detail, it will be apparent to one skilled in the art that various changes and modifications can be made and equivalents employed, without departing from the present invention. It is to be understood that the invention is not limited to the details of construction, the arrangements of components, the process of closing the PFO 2, and/or the sequence of operations for closing the PFO 2 set forth in the above description or illustrated in the drawings. Exemplary steps set forth in the method for closing the PFO 2 may be omitted as the practitioner sees fit. Further, the invention is not limited to the closure of a PFO 2. Other heart or tissue defects, such as atrial septal defects, may be closed utilizing the present invention. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A medical device comprising:
    a connector applicator including a slidable driver, said connector applicator including two longitudinally-spaced apertures defined therein;
    a plurality of staples held by said connector applicator;
    two discrete tethers each extending through a corresponding said aperture; and
    two discrete expandable anchors, each said anchor connected to a corresponding said tether, wherein said anchors are longitudinally spaced apart from one another relative to said connector applicator, and spaced apart from said connector applicator;
    wherein said connector applicator is configured to eject said staples substantially in a first direction, and wherein said driver is configured to move substantially in a second direction substantially perpendicular to said first direction.

2. The device of claim 1, wherein at least one said tether passes through one said aperture different from at least one other said tether.

3. The device of claim 1, further comprising a guidewire and a sheath having a lumen therethrough, said sheath slidable along said guidewire; wherein said connector applicator is sized to pass through said lumen of said sheath.

4. The device of claim 1, wherein at least one said anchor is elastically deformable.

5. The device of claim 1, wherein at least one said staple is plastically deformable.

6. The device of claim 1, further comprising a backbone interconnecting at least two said staples.

7. The device of claim 6, wherein at least part of said backbone is substantially flexible.

8. The device of claim 1, wherein said driver has a longitudinal passage defined therein, wherein the cross-section of said passage varies along at least part of its length, and wherein at least part of at least one said staple is positioned within said passage.

* * * * *